(12) United States Patent
Suzuki et al.

(10) Patent No.: US 8,663,089 B2
(45) Date of Patent: Mar. 4, 2014

(54) TREATMENT TOOL FOR ENDOSCOPE

(75) Inventors: Keita Suzuki, Tokyo (JP); Mamoru Nakada, Tokyo (JP)

(73) Assignee: Olympus Corporation, Tokyo (JP)

( * ) Notice: Subject to any disclaimer, the term of this patent is extended or adjusted under 35 U.S.C. 154(b) by 171 days.

(21) Appl. No.: 10/872,988

(22) Filed: Jun. 21, 2004

(65) Prior Publication Data
US 2005/0004432 A1 Jan. 6, 2005

(30) Foreign Application Priority Data

Jun. 24, 2003 (JP) ................................. 2003-179648
May 25, 2004 (JP) ................................. 2004-154682

(51) Int. Cl.
*A61B 1/00* (2006.01)
*A61B 17/00* (2006.01)

(52) U.S. Cl.
USPC .............................. 600/104; 600/106; 606/1

(58) Field of Classification Search
USPC ......... 600/101, 129, 137, 139, 142, 564, 104, 600/154, 106, 140; 606/205, 206, 207, 208, 606/209, 210, 211, 41, 42, 43, 44, 45, 46, 606/47, 48, 49, 50, 51, 52, 1, 100
See application file for complete search history.

(56) References Cited

U.S. PATENT DOCUMENTS

| | | | |
|---|---|---|---|
| 3,896,793 A * | 7/1975 | Mitsui et al. .................. | 600/104 |
| 4,294,254 A | 10/1981 | Chamness | |
| 5,228,451 A | 7/1993 | Bales et al. | |
| 5,254,130 A * | 10/1993 | Poncet et al. ................. | 606/206 |
| 5,275,614 A | 1/1994 | Haber et al. | |
| 5,308,357 A * | 5/1994 | Lichtman ....................... | 606/205 |
| 5,439,478 A * | 8/1995 | Palmer ........................... | 606/205 |
| 5,520,678 A * | 5/1996 | Heckele et al. ................. | 606/1 |
| 5,632,764 A * | 5/1997 | Beideman et al. ............. | 606/205 |
| 5,643,294 A * | 7/1997 | Tovey et al. ................... | 606/148 |
| 5,865,724 A * | 2/1999 | Palmer et al. ................. | 600/104 |
| 5,921,915 A * | 7/1999 | Aznoian et al. ............... | 600/104 |
| 6,010,523 A * | 1/2000 | Sabin et al. .................... | 606/205 |
| 6,203,533 B1 * | 3/2001 | Ouchi ............................ | 604/264 |
| 6,443,909 B1 * | 9/2002 | Ouchi ............................ | 600/562 |
| 6,514,197 B1 * | 2/2003 | Ouchi et al. .................. | 600/106 |
| 6,569,105 B1 * | 5/2003 | Kortenbach et al. .......... | 600/562 |
| 6,605,104 B2 * | 8/2003 | Sato et al. ...................... | 606/206 |
| 6,972,017 B2 * | 12/2005 | Smith et al. .................... | 606/47 |

(Continued)

FOREIGN PATENT DOCUMENTS

| | | |
|---|---|---|
| EP | 0 738 501 A1 | 10/1996 |
| JP | S56-63348 | 5/1981 |

(Continued)

*Primary Examiner* — Philip R. Smith
*Assistant Examiner* — Rynae Boler
(74) *Attorney, Agent, or Firm* — Scully, Scott, Murphy & Presser, P.C.

(57) ABSTRACT

A treatment tool for an endoscope, including: an insertion tube extending toward one direction; a movable tip member which is provided on a tip of the insertion tube and which is used for a treatment of a living organ; a control member of which a tip is connected to the insertion tube and controls the movable tip member by advancing and retracting a control shaft member inserted in the insertion tube; and a covering tube which covers at least one part of a circumference of the insertion tube. At least one part of the insertion tube rotates freely about an axis of the insertion tube.

8 Claims, 14 Drawing Sheets

(56) References Cited

U.S. PATENT DOCUMENTS

| | | | | |
|---|---|---|---|---|
| 7,186,261 | B2* | 3/2007 | Prestel | 606/208 |
| 7,931,667 | B2* | 4/2011 | Prestel et al. | 606/205 |
| 2001/0047124 | A1* | 11/2001 | Yamamoto | 600/101 |
| 2002/0133127 | A1* | 9/2002 | Collins | 604/264 |
| 2003/0009177 | A1* | 1/2003 | Middleman et al. | 606/127 |
| 2003/0195432 | A1* | 10/2003 | Kortenbach et al. | 600/562 |

FOREIGN PATENT DOCUMENTS

| | | |
|---|---|---|
| JP | S57-74018 | 5/1982 |
| JP | H5-21913 | 3/1993 |
| JP | H7-505801 | 6/1995 |
| JP | 8-126648 | 5/1996 |
| JP | H8-280701 | 10/1996 |
| JP | 9-507149 | 7/1997 |
| JP | H11-155878 | 6/1999 |

* cited by examiner

TREATMENT TOOL FOR ENDOSCOPE

Priority is claimed on Japanese Patent Application No. 2003-179648, filed Jun. 24, 2003, and Japanese Patent Application No. 2004-154682, filed May 25, 2004, the contents of which are incorporated herein by reference.

BACKGROUND OF THE INVENTION

1. Field of the Invention

The present invention relates to a treatment tool for an endoscope covered with a covering tube.

2. Description of Related Art

When clamping a living organ such as an affected part using a treatment tool such as forceps, etc., there is a case in which an open-and-closing direction of clamp pieces which is provided at a tip of the forceps and is placed in a body cavity differs from a direction toward the affected part to be clamped.

In such a case, a method to change the direction of the clamp pieces easily by rotating a shaft member such as a control wire, etc., keeping the clamp pieces inserted into the body cavity, is proposed (for example, refer to FIG. 3 of Published Japanese Translation No. 9-507149 of the PCT International Application, and FIG. 3 of U.S. Pat. No. 5,275,614).

On the other hand, there is also a case in which the forceps, which is used by inserting it into a channel for a treatment tool, is placed so that a direction of the clamp pieces are different from a direction toward an affected part, when the forceps is used by inserting it into the channel for a treatment tool.

The direction of the clamp pieces inside the body cavity must be changed before clamping.

SUMMARY OF THE INVENTION

A treatment tool for an endoscope of the present invention includes: an insertion tube extending toward one direction; a movable tip member which is provided on a tip of the insertion tube and which is used for a treatment of a living organ; a control member of which a tip is connected to the insertion tube and controls the movable tip member by advancing and retracting a control shaft member inserted in the insertion tube; and a covering tube which covers at least one part of a circumference of the insertion tube; wherein, at least one part of the insertion tube rotates freely about an axis of the insertion tube.

It is preferable that one of a covering tube side convexity and a covering tube side concavity be provided to at least one end, in the diameter direction, of the covering tube; a connection side concavity or a connection side convexity which can be joined with one of the covering tube side convexity and the covering tube side concavity, be provided to at least one of a bottom end of the movable tip member and a tip of the control member; and between the covering tube side convexity and the connection side concavity, or between the covering tube side concavity and the connection side convexity, be joined to each other so that they rotate freely about an axis of the covering tube.

It is preferable that the control shaft member be connected to the movable tip member so that the control shaft member freely rotates about an axis of the movable tip member.

It is preferable that a flange portion protruding outward in a diameter direction be provided to a tip of the control shaft member; a hole in which the flange portion joins, be provided to a bottom end of the movable tip member; a step which joins to a circumference of the flange portion so that the flange portion can rotate freely, be provided to an inner face of the hole; and a locking member which locks advancing movement along an axis direction of the control shaft member be provided.

It is preferable that the covering tube, the insertion tube, and the control shaft member be flexible.

DETAILED DESCRIPTION OF THE INVENTION

A first embodiment of a treatment tool for an endoscope according to the present invention will be explained below referring to FIGS. 1 to 5.

Figure 1:
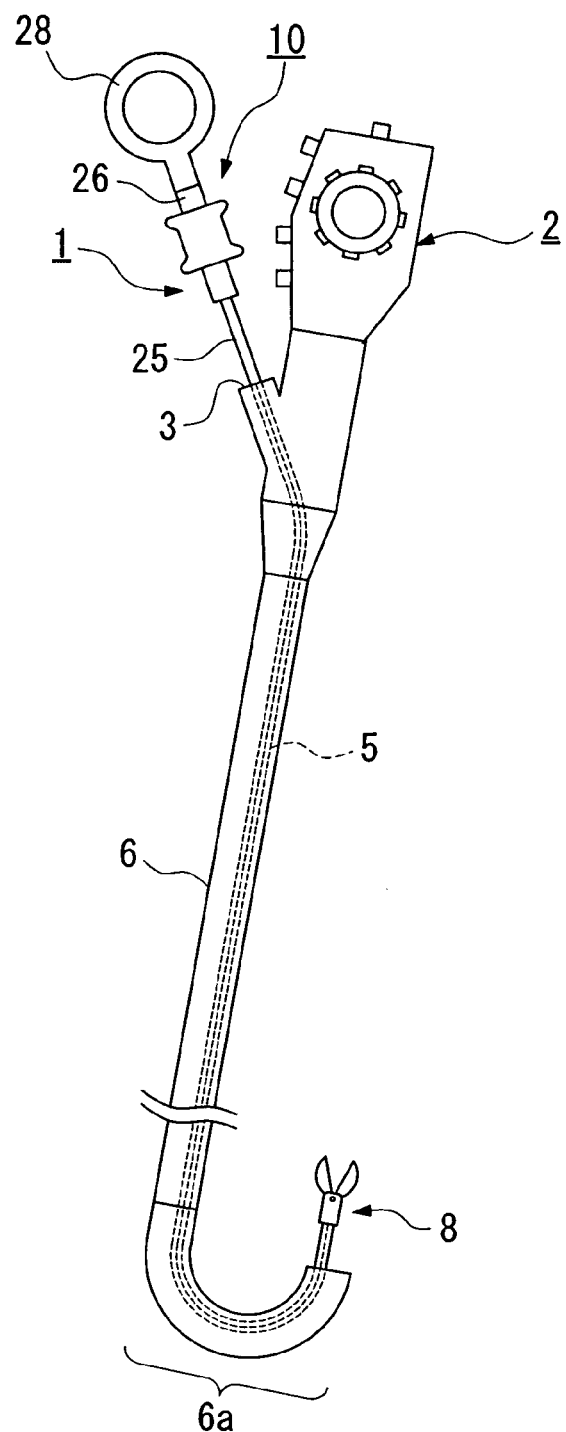
FIG. 1 is a plan view of a treatment tool for an endoscope according to the first embodiment of the present invention, inserted into a flexible endoscope.

As shown in FIG. 1, a forceps (the treatment tool for an endoscope) 1 of the present embodiment is inserted into a channel for a treatment tool 5 from a plug port 3 of the endoscope 2, then is used by inserting it into the body cavity together with an insertion part 6 of the fiberscope 2.

Figure 2:
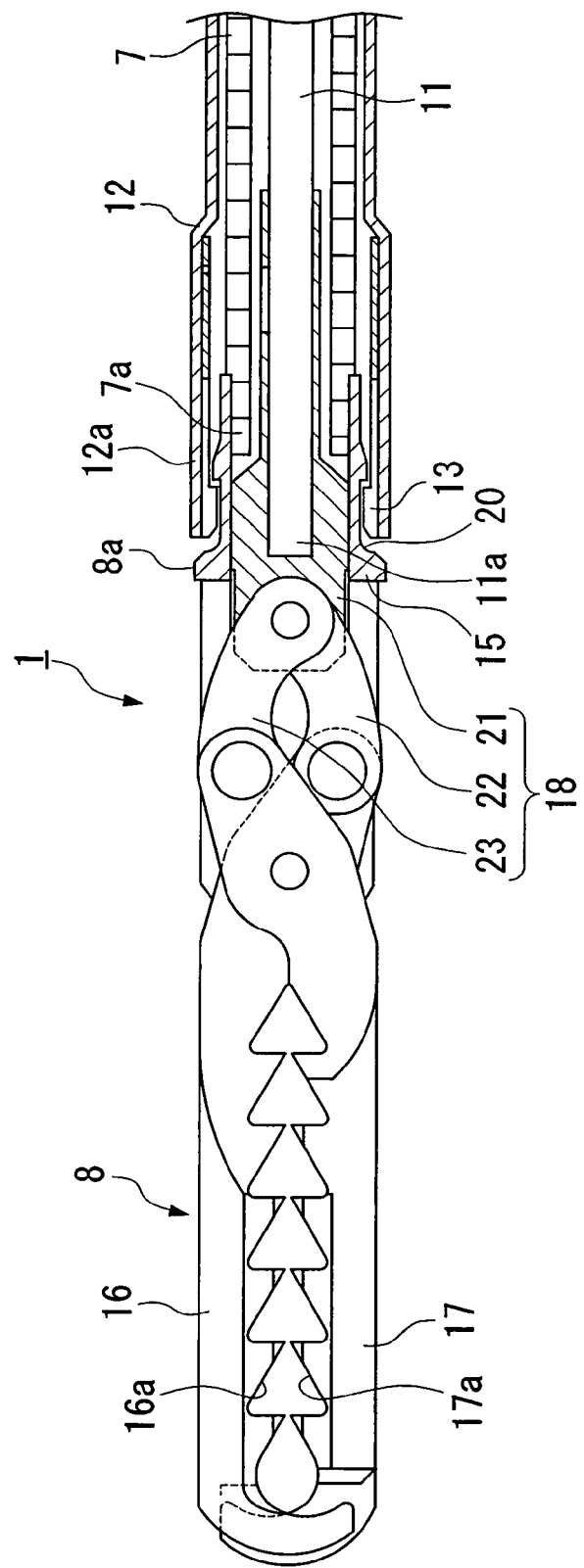
FIG. 2 is a side view of a tip side of the same treatment tool for an endoscope, shown partially in cross sectional view.

As shown in FIG. 2, the forceps 1 has an insertion tube 7 which is inserted into the channel for a treatment tool 5 and extends toward one direction, and a clamp member (movable tip member) 8 of which a bottom end 8a is connected to a tip end 7a of the insertion tube 7, and clamps a living organ.

Figure 3:
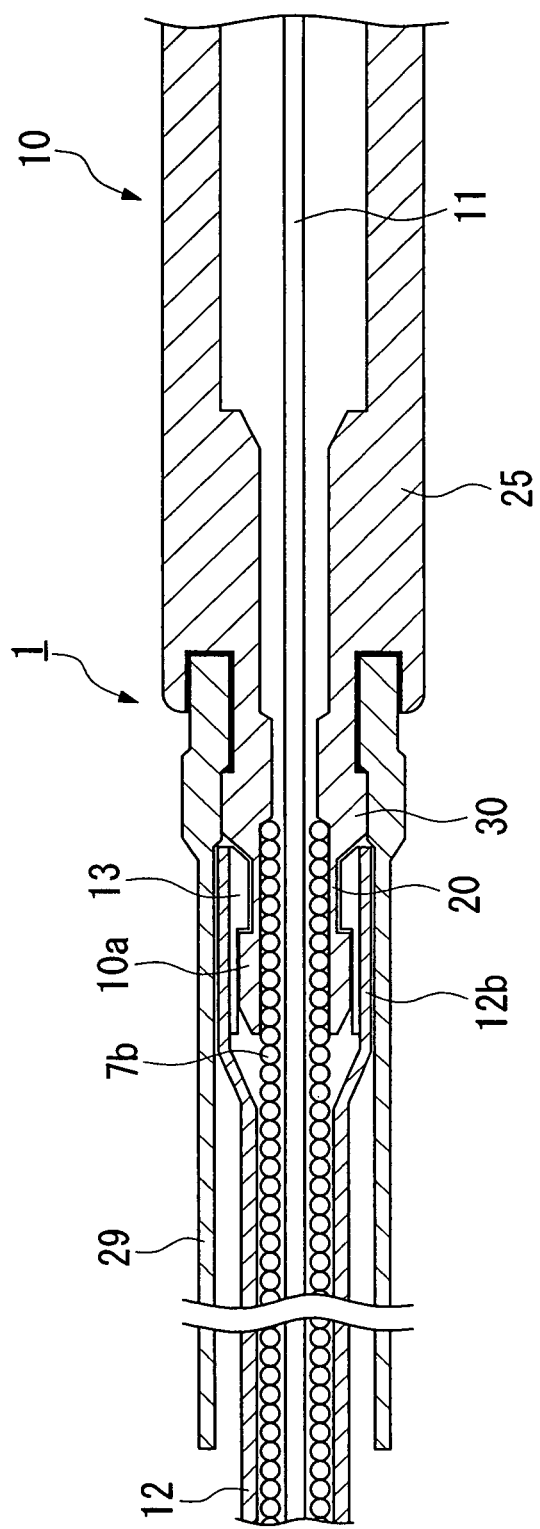
FIG. 3 is a cross sectional view of a bottom side of the same treatment tool for an endoscope.

As shown in FIG. 3, the forceps 1 has a control part 10 of which a tip 10a is connected to the bottom end 7b of the insertion tube 7 and controls the clamp member 8 by advancing and retracting a control shaft member 11 inserted inside the insertion tube 7. A circumference of the insertion tube 7 is covered with a covering tube 12.

The covering tube 12 is a resin product which is electrically insulating and is flexible. As shown in FIGS. 2 and 3, the covering tube 12 is connected to the forceps member 8 at a side of a tip 12a, and connected to the control part 10 at a side of a bottom end 12b. A covering tube side convexity 13 protruding toward the inside is formed inside the tip 12a and the bottom end 12b.

Figure 4:
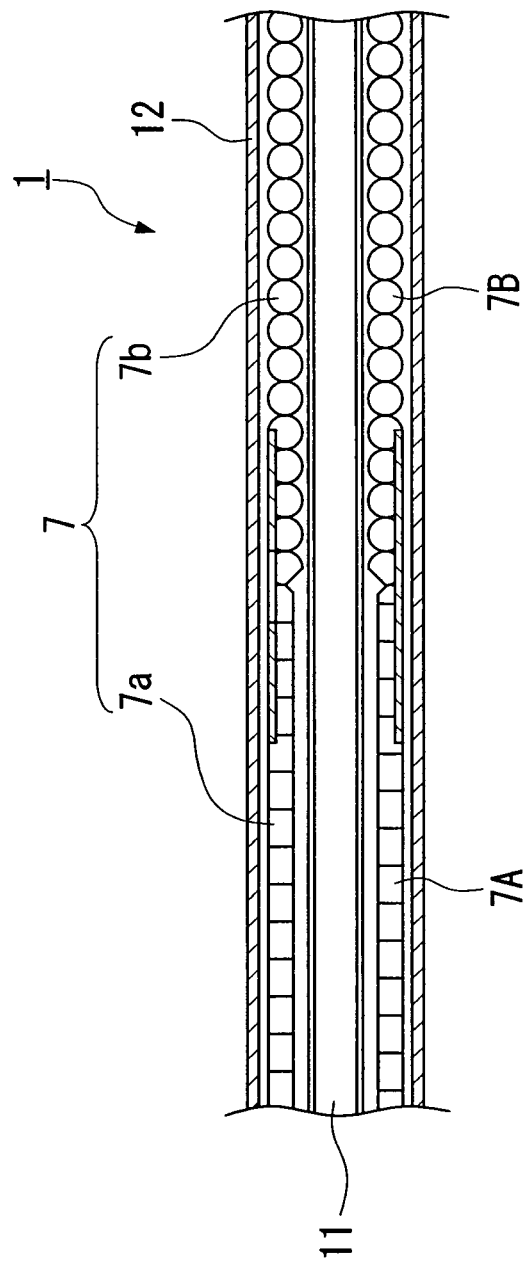
FIG. 4 is a partially cross sectional view of one part of the same treatment tool for an endoscope in section.

As shown in FIGS. 2 to 4, the insertion tube 7 includes a short-wind-pitch coil made of a steel wire, and constitutes a flexible tube. A side of the bottom end 7b of the steel wire has circular-shaped cross section 7A, and a side of the tip end 7a of the steel wire has square-shaped cross section 7B.

The short-wind-pitch coil is not limited to being made by winding a steel line in a spiral shape, and instead, a multiple winding coil made by winding a plurality of steel lines can be adopted as the short-wind-pitch coil. In this case, rotation-operability can be improved in comparison to the case of using one steel line.

As shown in FIG. 2, the clamp member 8 has a tip cover 15 which is connected to the tip end 7a of the insertion tube 7, a pair of clamp pieces 16 and 17 which face each other and are able to open and close, and a link mechanism 18 which converts a advancing and retracting action of the control shaft member 11 to an open-and-closing action of the pair of clamp pieces 16 and 17.

The side of bottom end 8a of the tip cover 15 is formed in a tubular shape, and is connected to the insertion tube 7 by connecting the insertion tube 7 to an inner face of the tip cover 15. On the other hand, a connection side concavity 20 which can connect to a covering tube side convexity 13 is formed along the circumference of the insertion tube 7 in a groove. The covering tube 12 and the tip cover 15 can freely rotate relative to each other around an axis of the covering tube 12, and are connected so that the advancing and retracting actions along the axis direction are restricted.

Each clamp piece 16 and 17 is formed as metal pieces having a rod shape extending from a bottom end to a tip, and each clamp face 16a and 17a is formed in a corrugated shape. These clamp faces 16a and 17a clamp an affected part.

The control shaft member 11 is made of a steel wire, and can transmit a power along an axis direction, and has flexibility.

The link mechanism 18 has a connection member 21 connected to the tip 11a of the control shaft member 11, and a relay member 22 which connects the clamp piece 16 and the connection member 21, and a relay member 23 which connects the clamp piece 17 and the connection member 21.

Figure 5:
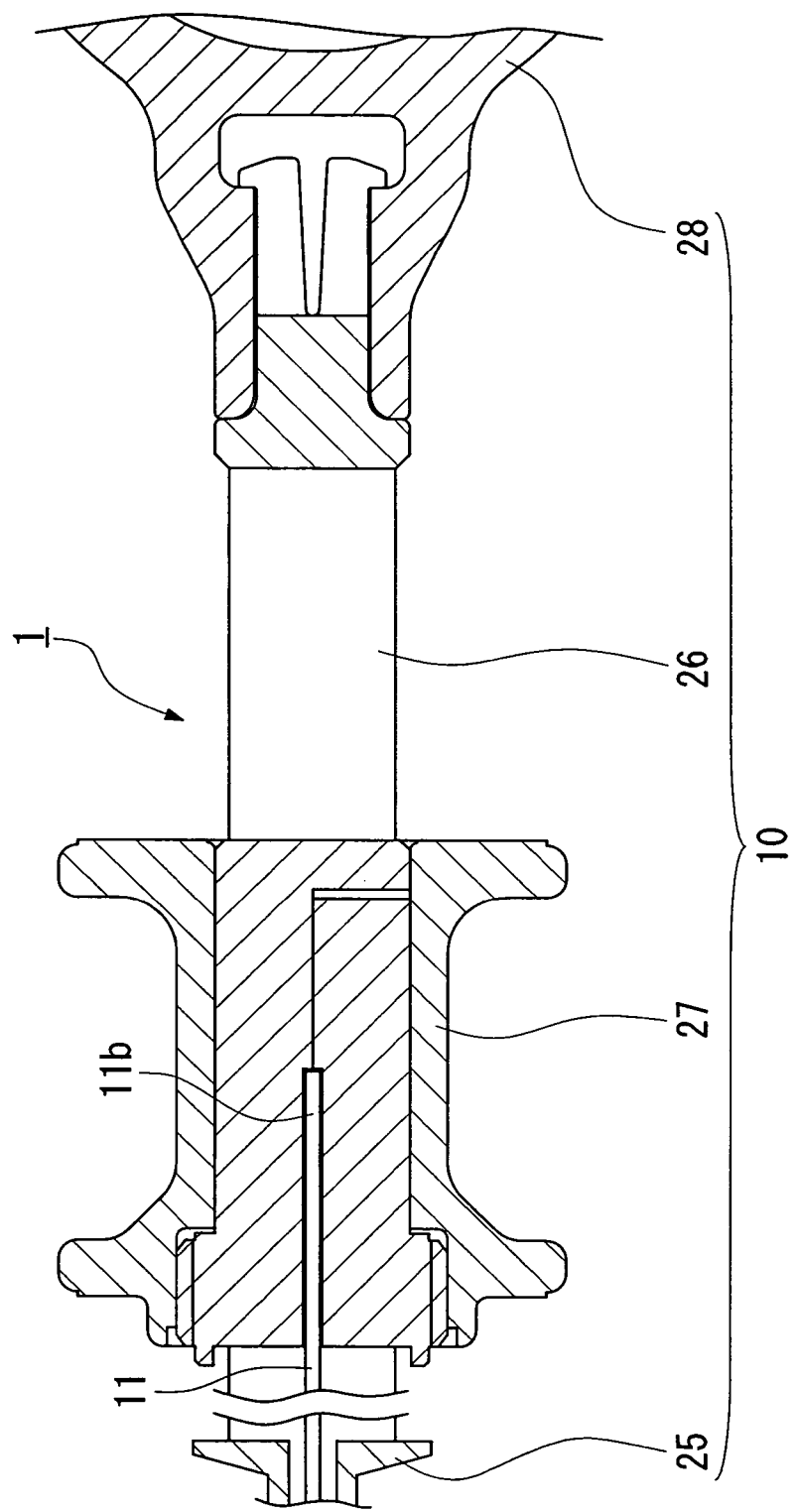
FIG. 5 is a cross sectional view of a control part of the same treatment tool for an endoscope.

As shown in FIGS. 3 and 5, the control shaft member 11 has a support member 25 which is connected to the bottom end 7b of the insertion tube 7, a slot member 26 in which the control shaft member 11 can be inserted into a center portion thereof, a slide member 27 which has a tubular shape and is placed to the circumference of the slot member 26 connected to the bottom end 11b of the shaft member 11 so that the slot member 26 can move along an axis direction, and a ring member 28 which is connected to a bottom end side of the slot member 26.

The tip side of the support member 25 has a tube 29 covering the bottom end 12b of the covering tube 12 from the outside thereof via a gap, and a convex shape portion 30 connected to the bottom end 12b. The covering tube 12 and the support member 25 are connected so that they are free to rotate relative to each other and also a movement along an axis direction is restricted.

The tube 29 made of a resin is fixed to the convex part 30. The tube 29 is arranged to the covering tube 12 via a gap, and is free to rotate around the axis of the covering tube 12.

Next, use of the forceps 1 of the present embodiment, having the constitution explained the above, will be explained.

First, as shown in FIG. 1, the endoscope 2 is inserted into a body cavity until the endoscope 2 reaches an affected part to be clamped.

Next, the forceps 1 is inserted from the plug port 3, and the clamp member 8 is exposed from a tip of the insertion part 6.

Then, a confirmation as to whether the open-and-closing direction of the pair of clamp pieces 16 and 17 match with a direction toward an affected part to be clamped, by observing them through the endoscope 2.

If the directions differ form each other, the support member 25 shown in FIG. 5 is rotated around an axis. At this time, the slot member 26 connected to the support member 25, the slide member 27, and the control shaft member 11 rotate in the same direction. On the other hand, the covering tube 12 holds a fixed position without rotation because the circumference of the covering tube 12 is pressed by an inner face of the plug port 3, and thus a large friction acts between them, and also a large friction acts between the covering tube 12 and the channel for a treatment tool 5.

At this time, if rotation torque is applied to the insertion tube 7 connected to the support member 25, the rotation torque is transferred to the tip end 7a through the bottom end 7b by twisting the insertion tube 7, because the covering tube side convexity 13 provided to the bottom end 12b of the covering tube 12 and the connection side concavity 20 of the support member 25 are connected so that they can freely rotate relative to each other.

At this time, because the covering tube side convexity 13 of the covering tube 12 and the connection side concavity 20 of the tip cover 15 are connected so that they can freely rotate relative to each other, the tip cover 15 rotates in the same direction with the insertion tube 7, then the clamp member 8 rotates in the same rotation direction with the slide member 27. In this way, the direction of the clamp member 8 can be matched with the direction toward the affected part to be clamped.

After that, the pair of clamp pieces 16 and 17 clamp the affected part by advancing and retracting the slide member 27.

In addition, even in the case in which a tip of the insertion member 6 of the endoscope 2 bends and the covering tube 12 is thereby pressed toward the inner face of the channel for a treatment tool 5, since the insertion tube 7 can be rotated with respect to the covering tube 12 by rotating the control member 10 as explained above, the direction of the clamp member 8 can be adjusted.

According to the forceps 1 explained the above, the insertion tube 7 can be freely rotated around its axis to the covering tube 12. Therefore, when the clamp member 8 connected to the insertion tube 7 needs to be rotated around its axis, the clamp member 8 can smoothly rotate in a desired direction even in the case in which friction occurs between the covering tube 12 and the external things contacting the covering tube 12, by rotating the control member 10 connected to the insertion tube 7 around its axis.

Next, the second embodiment of a treatment tool for an endoscope according to the present invention will be explained below referring to FIGS. 6 and 7. The same symbols will be applied to the same components explained in the above first embodiment, and explanations thereof are omitted in the following explanation.

The present embodiment differs from the above-mentioned first embodiment in the point that, in the present embodiment, the control shaft member 31 is connected to the connection member 32 and the slide member 33 so that the control shaft member 31 can freely rotate relative to each of the connection member 32 and the slide member 33, while in the first embodiment, the tip 11a of the control shaft member 11 is connected to the connection member 21 of the link mechanism 18 and also the bottom end 11b is connected to the slide member 27 of the control member 10.

Figure 6:
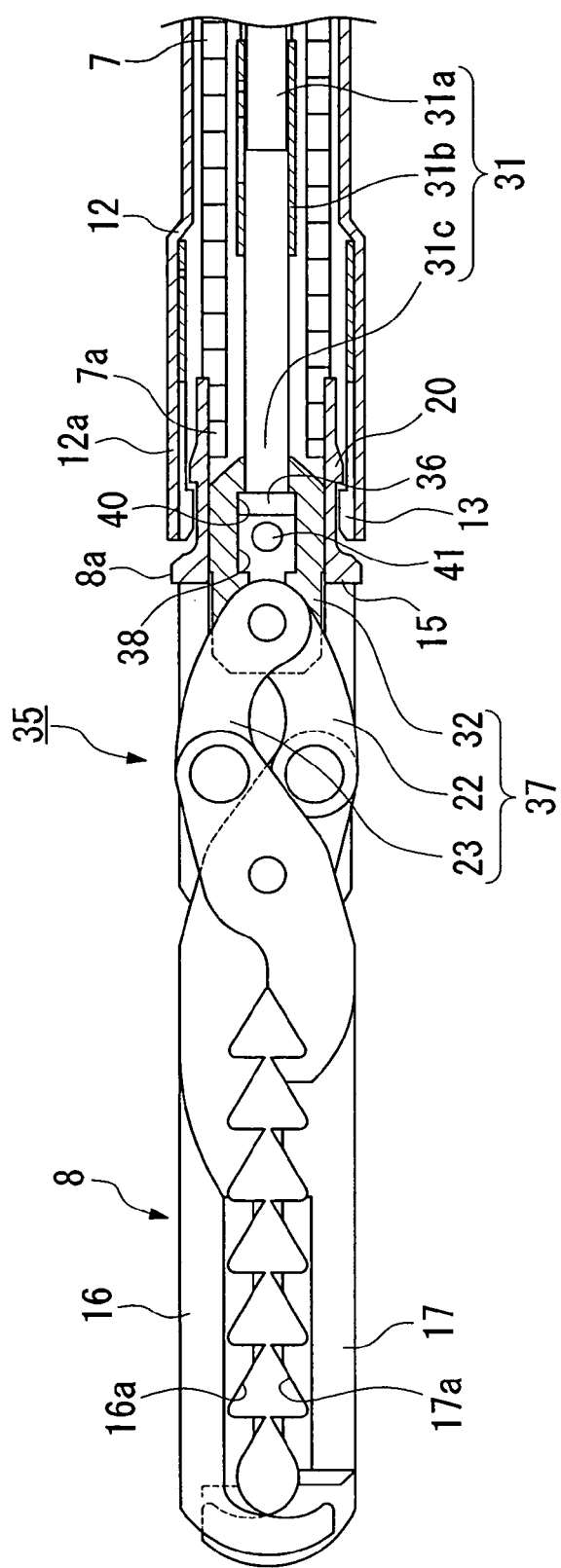
FIG. 6 is a side view of a tip side of a treatment tool for an endoscope according to the second embodiment of the present invention, shown partially in cross sectional view.

As shown in FIG. 6, the control shaft member 31 of a forceps 35 has a wire 31a made of a steel, and a shaft member 31c which has a rod-shape and is made of a stainless steel and is connected to the tip via a connection tube 31b.

A flange member 36 protruding outwardly in the diameter direction is provided to the tip of the shaft member 31c. A hole 38 in which the flange member 36 engages is provided to the connection member 32 of the link mechanism member 37 of the forceps member 8. By connecting the flange member 36 into the hole 38, the control shaft member 31 and the clamp member 8 are joined so that they can freely rotate relative to each other.

A step portion 40 to which the flange member 36 is joined by contacting to a circumference of the flange member 36 so that the flange member 36 can freely rotate, is provided inside of the hole 38. In addition, lock pin (lock member) 41 which stops advancing movement of the control shaft member 31 along the axis direction is provided in the hole 38.

Figure 7:
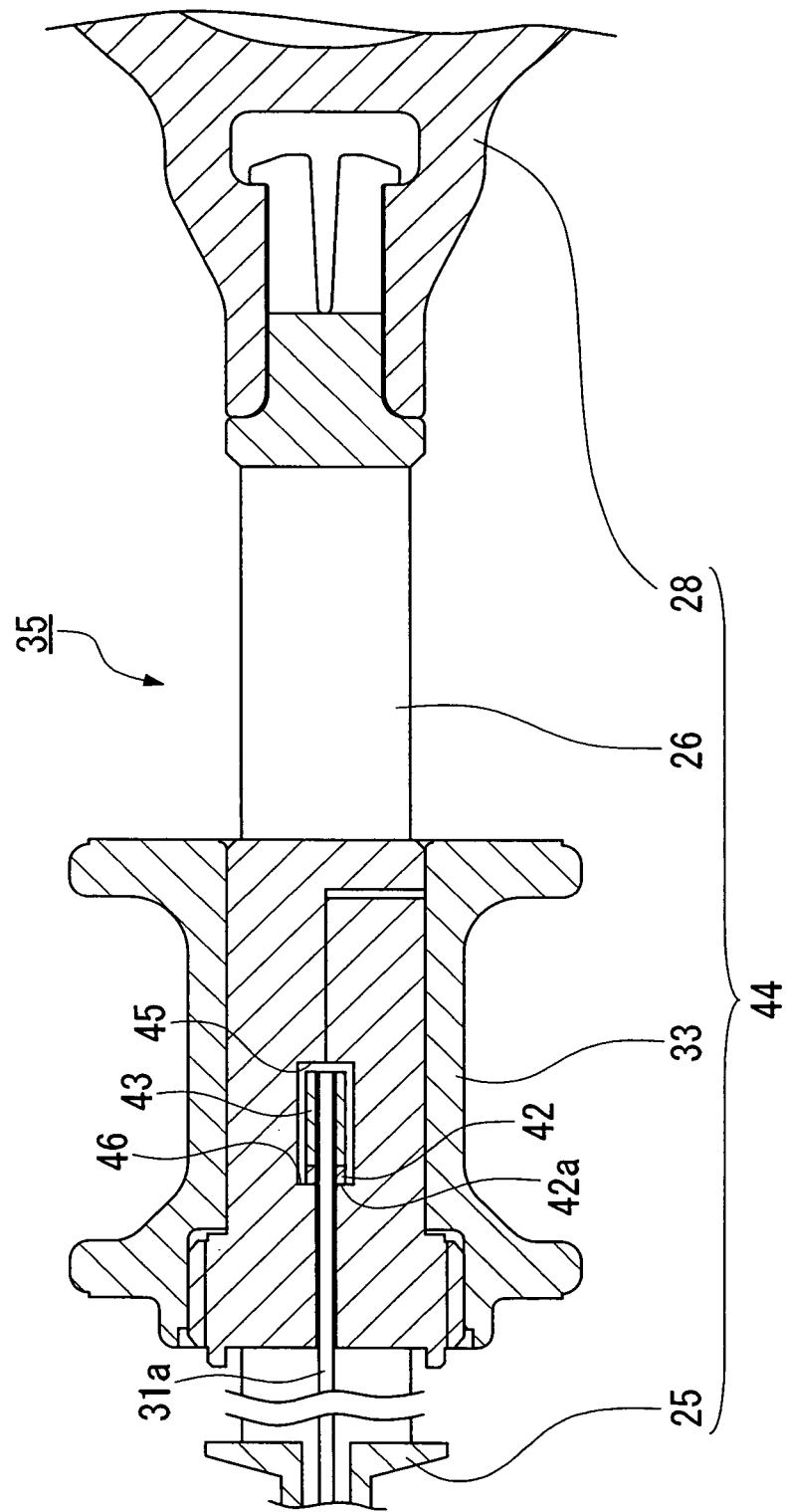
FIG. 7 is a cross sectional view of a control part of the same treatment tool for an endoscope.

As shown in FIG. 7, at a bottom end of the wire 31a of the control shaft member 31, a ring member 42 having larger diameter than that of the wire 31a, and a short tube member 43 are arranged in line along the axis direction. The short tube member 43 is connected to the bottom end of the wire 31a. The ring member 42 is arranged on the tip side relative to the short tube member 43 so that the ring member 42 can move in forward-and-backward directions and can freely rotate around the axis relative to the wire 31a. The slide member 33 of the control member 44 has a slide hole 45 in which these ring members 42 and short tube member 43 are inserted. A step 46 which connects to a tip side end face 42a of the ring member 42 is formed inside the slide hole 45.

The ring member 42 and the step 46 are joined so that these can freely rotate relative to each other.

Next, use of the forceps 35 of the present embodiment having the constitution explained above will be explained in the following.

The forceps 35 of the present embodiment is inserted into the endoscope 2 and is used together with the endoscope 2 in the same manner as the forceps 1 of the first embodiment mentioned above.

Then, if a direction of a clamp member 8 differs with a direction toward the affected part to be clamped, the support member 25 shown in FIG. 7 is rotated around its axis.

In this case, in the same manner as in the above-mentioned first embodiment, the covering tube 12 holds the fixed position without rotation because the circumference of the covering tube 12 is pressed by an inner face of the plug port 3, and then a large friction works between them. On the other hand, because the covering tube side convexity 13 of the covering tube 12 and the connection side concavity 20 are connected so that they can freely rotate relative to each other, the slot member 26 and the insertion tube 7 connected to the support member 25 rotates in the same direction with the support member 25.

At this time, the slide member 33 rotates following the rotation of the slot member 26. However, the short tube member 43 will not rotate even though at least one of the slide member 33 and the ring member 42 rotates, because the ring member 42 of the control shaft member 31 and the step 46 of the slide hole 45 are joined so that they can freely rotate relative to each other. Therefore, the control shaft member 31 will not rotate because a rotation torque is not transferred from the control member 44 to the operation shaft member 31.

In addition, the control shaft member 31 will not rotate even in the case in which a rotation torque is transferred to the bottom end of the tip cover 15 via the insertion tube 7, because, at the link mechanism 37, the flange member 36 and hole 38 are joined so that they can freely rotate relative to each other, and thus the rotation torque will not be transferred from the tip cover 15 to the axis member 31c.

Therefore, the rotation torque required to rotate the support member 25 can be minimized when the direction of clamp member 8 is adjusted to the direction toward the affected part to be clamped, because the control shaft member 31 will not rotate.

At the forceps 35, between the step 40 inside the hole 38 and the lock pin 41 are joined with the flange member 36 arranged between them. Therefore, by controlling an advancing and retracting operation of the control shaft member 31, a power is transferred from the flange portion 36 to the link mechanism 18 via the step 40 and the lock pin 41, and then the clamp member 8 can be controlled. On the other hand, the control shaft member 31 will not produce resistance when the insertion tube 7 is rotated, because the control shaft member 31 will not follow the rotation of the insertion tube 7 and the clamp member 8 when rotating the insertion tube 7 to the covering tube 12 around its axis. Therefore, the transmission of the rotation torque from the insertion tube 7 to the clamp member 8 can be improved because the torque of the insertion tube 7 can be transferred to the clamp member 8 more easily.

Figure 14:
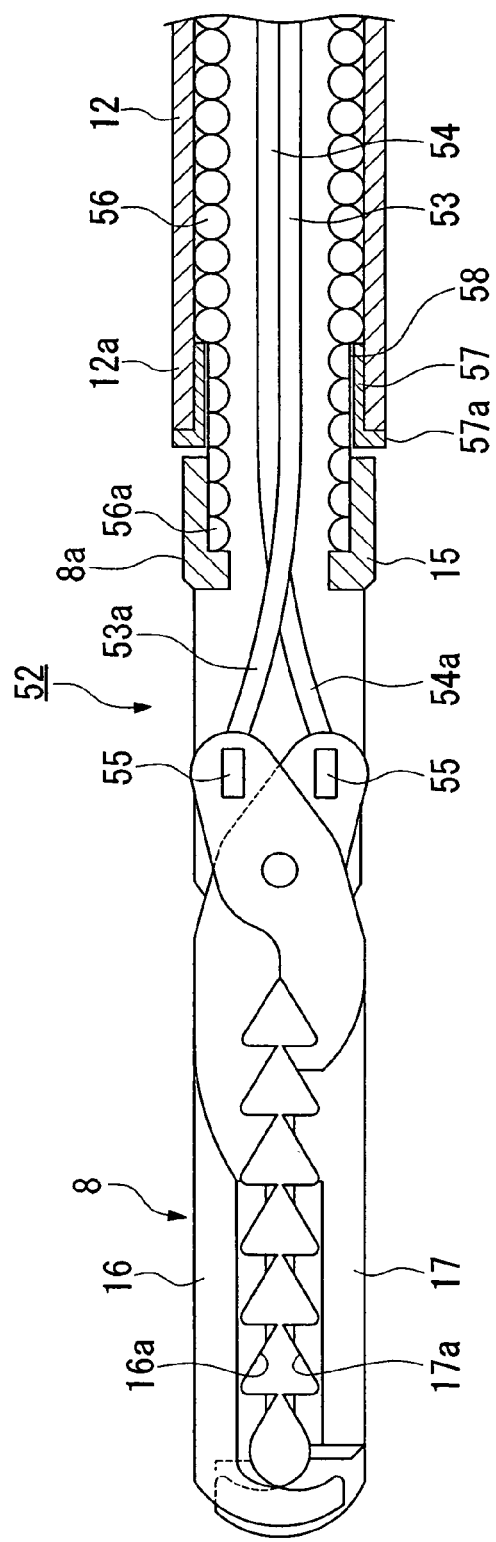
FIG. 14 is a side view of a tip side of a treatment tool for an endoscope according to the third embodiment of the present invention, shown partially in cross sectional view.
Figure 15:
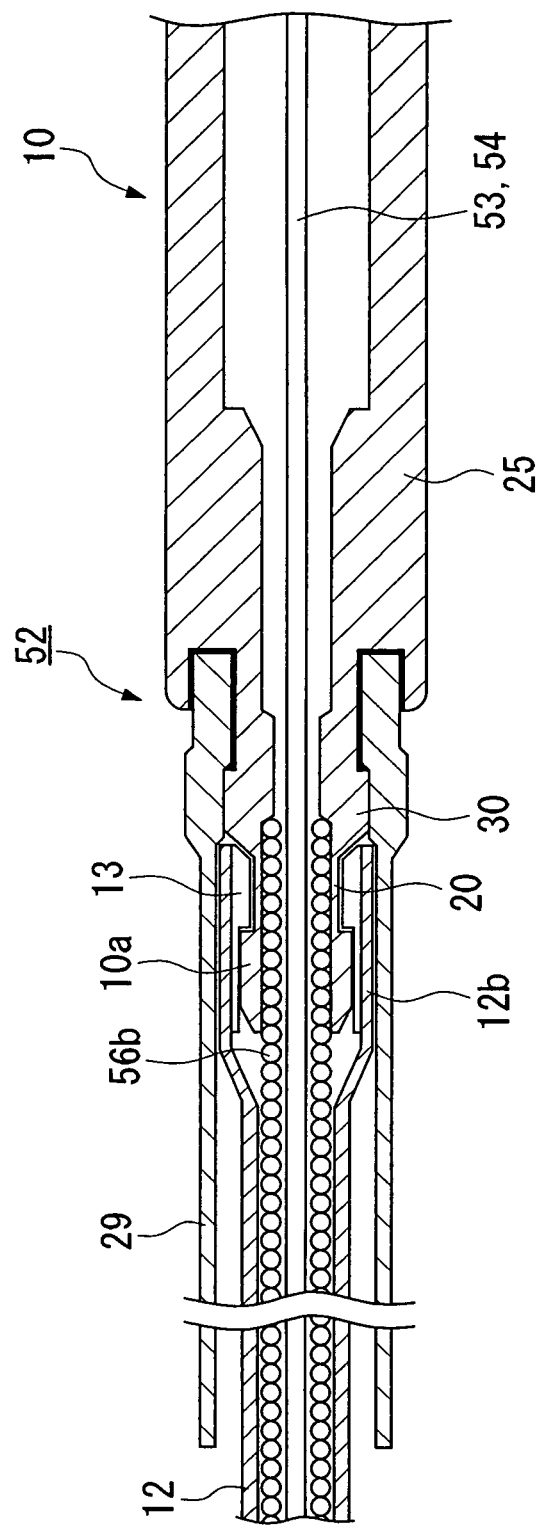
FIG. 15 is a cross sectional view of a bottom end side of the same treatment tool for an endoscope.
Figure 16:
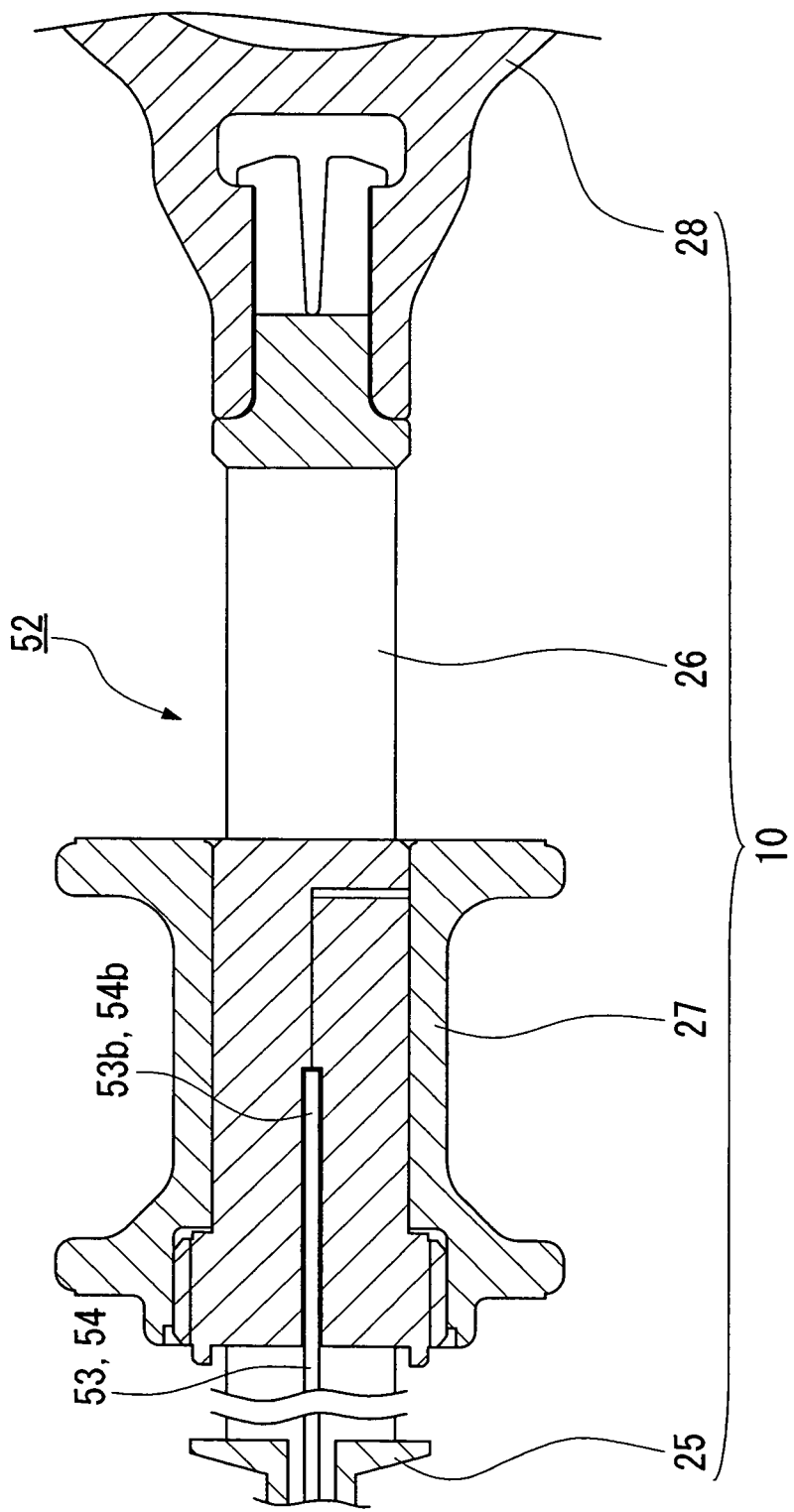
FIG. 16 is a cross sectional view of a control part of the same treatment tool for an endoscope.

Next, the third embodiment of a treatment tool for an endoscope according to the present invention will be explained below referring to FIGS. 14 to 16. The same symbols will be applied to the same components explained in the above first embodiment, and explanations thereof are omitted in the following explanation.

The present embodiment differs from the above-mentioned first embodiment in the following points.

The first point is that a control shaft member of a forceps 52 of the present embodiment is composed by control shaft members 53 and 54 made of two steel wires, while the control shaft member 11 of the first embodiment is made of one steel wire.

The second point is that the forceps 52 of the present embodiment is provided with a link mechanism 55 including the control shaft members 53 and 54 each directly connected with the clamp pieces 17 and 16 at distal ends 53a and 54a thereof, while the link mechanism 18 of the forceps of the first embodiment is provided with the connection member 21 and the relay member 22 and 23.

The third point is that an insertion tube 56 of the forceps 52 of the present embodiment is made of one short-wind-pitch coil having circular-shaped cross section, while the insertion tube 7 of the forceps 1 of the first embodiment has circular-shaped cross section 7A at the side of the tip end 7a and square-shaped cross section 7B at the side of the bottom end 7b.

The fourth point is that a covering tube side convexity 57 of the forceps 52 of the present embodiment has an outwardly protruded portion 57a formed so that one portion thereof is exposed outwardly at the distal end portion of the covering tube 12, while the covering tube side convexity 13 of the forceps 1 of the first embodiment is arranged inside the distal end portion of the covering tube 12. Between the covering tube 12 and the covering tube side convexity 57 are fixed by adhesive or by friction resistance between contact parts of the covering tube 12 and the covering tube side convexity 57.

The fifth point is that a connection side concavity 58 of the forceps 52 of the present embodiment is formed as a small diameter part formed on a periphery of a distal portion of an insertion tube 56, while the connection side concavity 20 of the forceps 1 of the first embodiment is formed on the tip cover 15.

Use of the forceps 52 of the present embodiment having the above-mentioned embodiment is same as the forceps 1 of the first embodiment, and explanation thereof is omitted here.

According to the forceps 52 of the present embodiment, complicated link mechanism is unnecessary and a cost reduction in its manufacturing is possible because the forceps 52 adopts the link mechanism 55 including the control shaft members 53 and 54 each directly connected with the clamp pieces 17 and 16 at distal ends 53a and 54a thereof.

In addition, further cost reduction in the manufacturing is possible by adopting the insertion tube 56 made of one short-wind-pitch coil having the same cross section shape at any location in the length direction.

Furthermore, as the outwardly protruded portion 57a is formed at the distal end portion of the covering tube side convexity 57, when joining between the covering tube 12 and the covering tube side convexity 57, an adhesive will not overcome the outwardly protruded portion 57a and will not overflow toward another portion. Therefore, the forceps 52 can be manufactured by an easy manufacturing method. Also, in the case in which joining between the covering tube 12 and the outwardly protruded portion 57a using friction resistance, the forceps 52 can be manufactured by an easy manufacturing method, because the covering tube side convexity 57 can be joined with the covering tube 12 by inserting the covering tube side convexity 57 into the covering tube 12 until the covering tube 12 contacts with the outwardly protruded portion 57a. Furthermore, as the connection side concavity 58 is formed at the distal end portion of the insertion tube 56, the number of necessary parts for the manufacturing is minimized, and thus further cost reduction in the manufacturing becomes possible.

While preferred embodiments of the invention have been described and illustrated as above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

Figure 8:
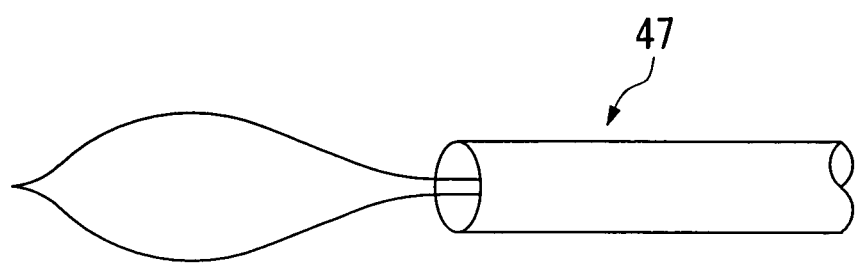
FIG. 8 is a side view of a tip of a treatment tool for an endoscope according to another embodiment of the present invention.
Figure 9:
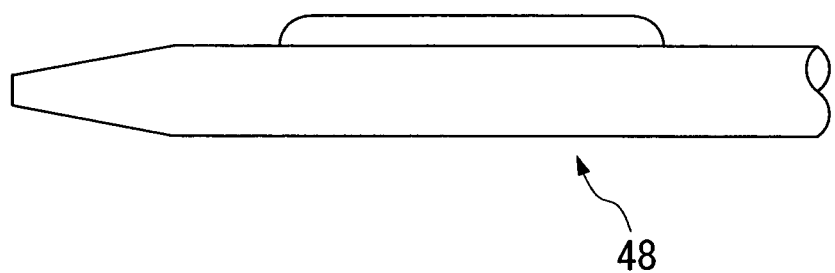
FIG. 9 is a side view of the tip of the same treatment tool for an endoscope.

For example, in each of the above-mentioned embodiments, a forceps is shown as one example of the treatment tool for endoscope, and also a clamp member for clamping a living organ is shown as one example of the movable tip member. However, the treatment tool for an endoscope is not limited to the forceps, and a knife (refer to FIG. 8) 47 or a papillotome (refer to FIG. 9) 48 which performs clamping or makes incisions, etc., by turning the direction in a body cavity during treatment can be applied.

Furthermore, in the above embodiments, the covering tube side convexity 13 is provided on the side of the covering tube 12, and the connection side concavity 20 is provided on the side of the clamp member 8 and the control members 10 and 44. However, this invention is not limited to this constitution, the connection side concavity may be provided on the side of the covering tube, and also the connection side concavities may be provided on the side of the control member and the clamp member.

Figure 10:
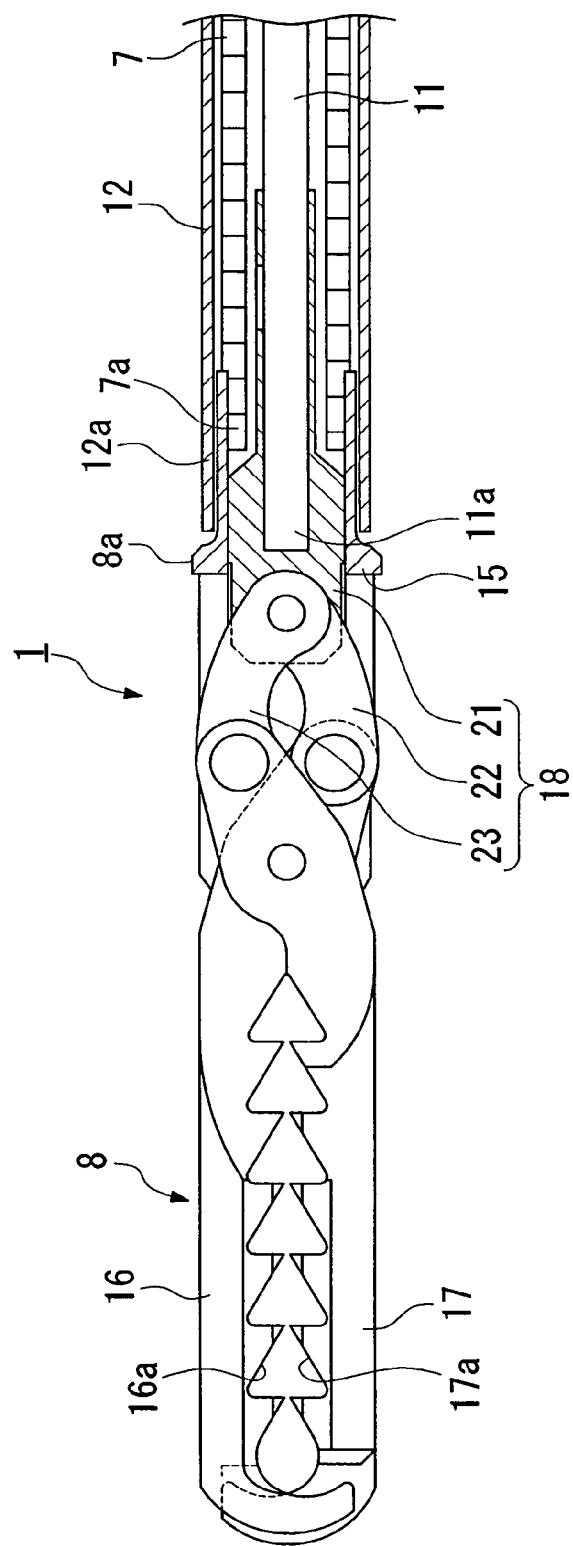
FIG. 10 is a side view of a tip side of the same treatment tool for an endoscope, shown partially in cross sectional view.
Figure 11:
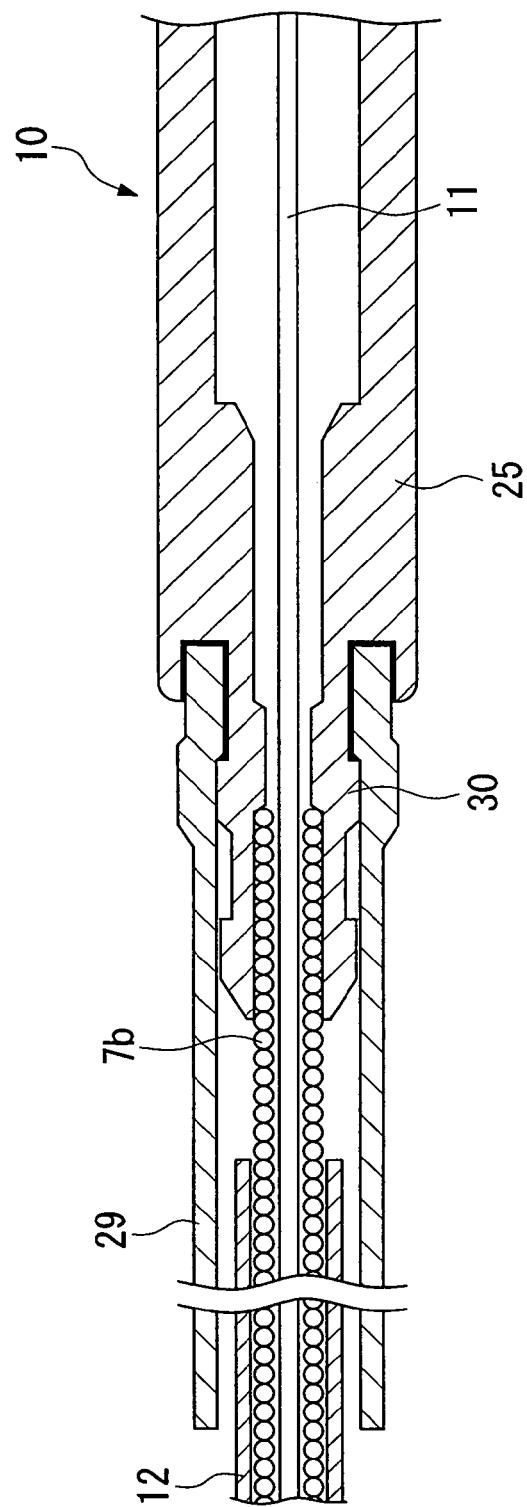
FIG. 11 is a cross sectional view of a bottom end side of the same treatment tool for an endoscope.

In addition, as shown in FIG. 10, a convexity and a concavity are not always necessary for the tip 12a of the covering tube 12 and for the bottom end 8a of the clamp member 8. Also, as shown in FIG. 11, a convexity and a concavity are not always necessary for the bottom end 12b of the covering tube 12 and for the convex part 30 of the control member 10. Furthermore, combination of these can also be adopted.

Figure 12:
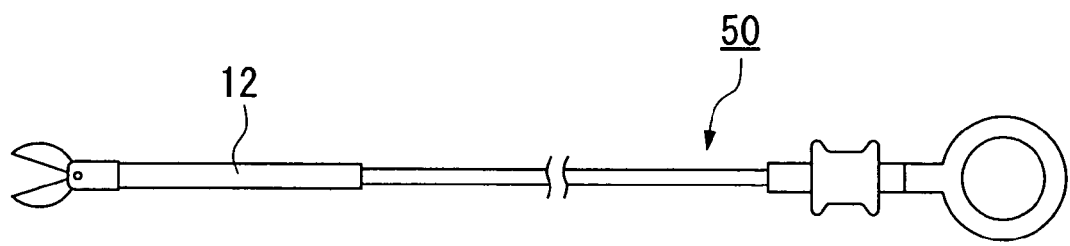
FIG. 12 is a plan view of the same treatment tool for an endoscope.
Figure 13:
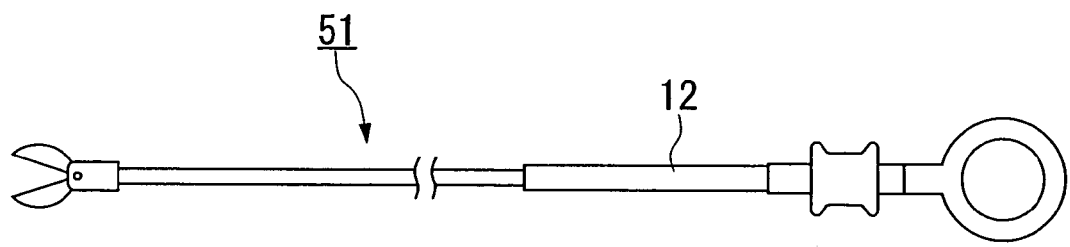
FIG. 13 is a plan view of the same treatment tool for an endoscope.

The covering tube 12 is not limited to one extending along the entire length of the insertion tube. For example, like a forceps 50 shown in FIG. 12, the covering tube 12 may be provided only at a location (for example, a location between a tip of the forceps 50 and a point 300 mm from the forceps 50) corresponding to a tip side bending part 6a of the endoscope 2 where a bending curvature is smallest within the insertion tube 6 of the endoscope 2, and a friction between the treatment tool and the channel is high. In addition, like a forceps 51 shown in FIG. 13, the covering tube 12 may be provided only for a location (for example at a location between the bottom end of the clamp 51 and a point 500 mm from the forceps 51) where the treatment tool and the plug port 3, which is a so-called rubber stopper, contact each other and produce high friction.

As explained above, the treatment tool for an endoscope of the present invention includes: an insertion tube extending toward one direction; a movable tip member which is provided on a tip of the insertion tube and which is used for a treatment of a living organ; a control member of which a tip is connected to the insertion tube and controls the movable tip member by advancing and retracting a control shaft member inserted in the insertion tube; and a covering tube which covers at least one part of a circumference of the insertion tube; wherein, at least one part of the insertion tube rotates freely about an axis of the insertion tube.

According to the treatment tool for an endoscope, the insertion tube can freely be rotated around an axis relative to the covering tube. Therefore, when the movable tip member connected to the insertion tube is rotated around the axis by rotating, the control member connected to the insertion tube is rotated around the axis. Then, the movable tip member can smoothly be adjusted toward a desired direction because a rotation torque is transferred to the movable tip member via the insertion tube even in the case in which friction is generated between the covering tube and the externals contacting the covering tube.

It is preferable that one of a covering tube side convexity and a covering tube side concavity be provided to at least one end, in the diameter direction, of the covering tube; a connection side concavity or a connection side convexity which can be joined with one of the covering tube side convexity and the covering tube side concavity, be provided to at least one of a bottom end of the movable tip member and a tip of the control member; and the covering tube side convexity and the connection side concavity, or the covering tube side concavity and the connection side convexity, are joined to each other so as to be rotatable about an axis of the covering tube.

In this case, connection ability and rotation-control ability can be improved by a simple constitution such as a connection of a convexity and a concavity.

It is preferable that the control shaft member be connected to the movable tip member so that the control shaft member freely rotates about an axis of the movable tip member.

In this case, the control shaft member can be held so that it will not follow a rotation of the insertion tube and the movable tip member when the insertion tube is rotated around an axis relative to the covering tube. Therefore, the rotation torque of the insertion tube can be transferred to the movable tip member more effectively because the control shaft member will not produce resistance against rotation control when the insertion tube is rotated, and then only the insertion tube can be rotated.

It is preferable that a flange portion protruding outward in a diameter direction be provided to a tip of the control shaft member; a hole in which the flange portion joins, be provided to a bottom end of the movable tip member; a step which joins to a circumference of the flange portion so that the flange portion can rotate freely, be provided to an inner face of the hole; and a locking member which locks advancing movement along an axis direction of the control shaft member be provided.

In this case, a transfer ability of a rotation torque toward the movable tip member of the insertion tube can be improved because the movable tip member and the control shaft member can independently rotate around an axis without losing a control ability of the movable tip member when it is controlled by advancing and retracting control of the control shaft member via the connection between the step and the flange portion.

It is preferable that the covering tube, the insertion tube, and the control shaft member be flexible.

In this case, the treatment tool for an endoscope can be used together with a flexible endoscope because the treatment tool for an endoscope can follow the bending of the insertion tube of the flexible endoscope. In addition, even in the case in which the circumference of the insertion tube is clamped by a port for a treatment tool, the movable tip member can easily be rotated by a rotation control of the insertion tube. Furthermore, even in the case in which the rotation control of the covering tube is difficult due to bending of the insertion tube, the movable member can easily be rotated by a rotation control of the insertion tube.

According to the treatment tool for an endoscope of the present invention, the movable tip member connected to a tip of the insertion tube can be independently rotated with respect to the covering tube by rotating the insertion tube around the axis, even though the periphery of the insertion tube is covered with the covering tube which is difficult to control the rotation around an axis. Therefore, torque transferring ability and controlling ability can be improved compared to controlling the rotation of the insertion tube.

What is claimed is:

1. A treatment tool for an endoscope, comprising:
   an insertion tube which is flexible and extends toward one direction;
   a movable tip member which is provided on a tip of the insertion tube and which is used for a treatment of a living organ;
   a control shaft member which is inserted into the insertion tube and which is connected to a proximal end of the movable tip member;
   a control member which is connected to a proximal end of the insertion tube and controls the movable tip member; and
   a covering tube which is flexible, and covers the insertion tube, wherein
   the insertion tube and the movable tip member are capable of together freely rotating relative to the covering tube around an axis of the covering tube, and
   the proximal end of the movable tip member and the covering tube are engaged with each other so as to restrict the proximal end of the movable tip member from advancing and retreating in an axis direction of the covering tube.

2. The treatment tool for an endoscope according to claim 1, wherein
   one of a covering tube side convexity which protrudes in a diameter direction of a distal end of the covering tube, and a covering tube side concavity which is concaved in the diameter direction of the distal end of the covering tube, is provided at the distal end of the covering tube;
   a connection side concavity which is capable of being joined with the covering tube side convexity, or a connection side convexity which is capable of being joined with the covering tube side concavity, is provided at the proximal end of the movable tip member; and
   the covering tube side convexity and the connection side concavity, or the covering tube side concavity and the connection side convexity, are joined to each other so as to be rotatable about the axis of the covering tube.

3. The treatment tool for an endoscope according to claim 1, wherein said control shaft member is connected to said movable tip member so that said control shaft member freely rotates about an axis of said movable tip member.

4. The treatment tool for an endoscope according to claim 3,
   wherein a flange portion protruding outward in a diameter direction is provided to a tip of said control shaft member;
   a hole in which said flange portion joins, is provided to a bottom end of said movable tip member;
   a step which joins to a circumference of said flange portion so that said flange portion can rotate freely, is provided to an inner face of said hole; and
   a locking member which locks advancing movement along an axis direction of said control shaft member is provided.

5. The treatment tool for an endoscope according to claim 1, wherein said covering tube, said insertion tube, and said control shaft member are flexible.

6. The treatment tool for the endoscope according to claim 1, wherein the insertion tube is covered with the covering tube from the distal end to the proximal end thereof.

7. The treatment tool for the endoscope according to claim 1, wherein
   the insertion tube and the control member are capable of freely rotating relative to each other around the axis direction of the covering tube, and are engaged so as to restrict the insertion tube and the control member from advancing and retreating in the axis direction of the covering tube.

8. The treatment tool for the endoscope according to claim 1, wherein
   the insertion tube is inserted into a channel for a treatment tool of the endoscope,
   the insertion tube is positioned at least inside the channel for the treatment tool, and
   the control member and the insertion tube are fixed such that the insertion tube rotates in accordance with rotation of the control member.

* * * * *